United States Patent
Florio

(10) Patent No.: US 7,092,755 B2
(45) Date of Patent: Aug. 15, 2006

(54) SYSTEM AND METHOD OF CARDIAC PACING DURING SLEEP APNEA

(75) Inventor: Joseph J. Florio, La Canada, CA (US)

(73) Assignee: Pacesetter, Inc., Sylmar, CA (US)

( * ) Notice: Subject to any disclaimer, the term of this patent is extended or adjusted under 35 U.S.C. 154(b) by 533 days.

(21) Appl. No.: 10/392,128

(22) Filed: Mar. 18, 2003

(65) Prior Publication Data

US 2004/0186523 A1    Sep. 23, 2004

(51) Int. Cl.
*A61N 1/36* (2006.01)

(52) U.S. Cl. .............................. 607/9; 607/2; 128/898

(58) Field of Classification Search .................... 607/2, 607/9; 600/26; 128/898
See application file for complete search history.

(56) References Cited

U.S. PATENT DOCUMENTS

| | | | |
|---|---|---|---|
| 5,335,657 A | 8/1994 | Terry, Jr. et al. | 607/45 |
| 6,126,611 A | 10/2000 | Bourgeois et al. | 600/529 |
| 6,314,324 B1 | 11/2001 | Lattner et al. | 607/42 |
| 6,415,183 B1 | 7/2002 | Scheiner et al. | 607/42 |
| 6,574,507 B1* | 6/2003 | Bonnet | 607/20 |
| 6,904,320 B1* | 6/2005 | Park et al. | 607/17 |
| 2002/0072781 A1 | 6/2002 | Lattner et al. | 607/42 |
| 2002/0193697 A1 | 12/2002 | Cho et al. | 600/529 |
| 2003/0195571 A1* | 10/2003 | Burnes et al. | 607/9 |

FOREIGN PATENT DOCUMENTS

| | | |
|---|---|---|
| EP | 0940155 A2 | 9/1999 |
| EP | 0940155 A3 | 5/2000 |
| EP | 1413330 A1 | 10/2003 |
| WO | WO 92/19318 | 11/1992 |
| WO | WO 00/01438 | 1/2000 |

* cited by examiner

*Primary Examiner*—Robert Pezzuto
*Assistant Examiner*—Yun Haeng Lee

(57) ABSTRACT

An exemplary method for treating sleep apnea is described that includes determining parameters for a cardiac pacing pulse based, at least in part, on information characteristic of sleep apnea, wherein the cardiac pacing pulse aims to create a hemodynamic imbalance. An exemplary implantable cardiac device is programmable to perform such an exemplary method. Other exemplary methods, devices, and/or media are also disclosed.

22 Claims, 10 Drawing Sheets

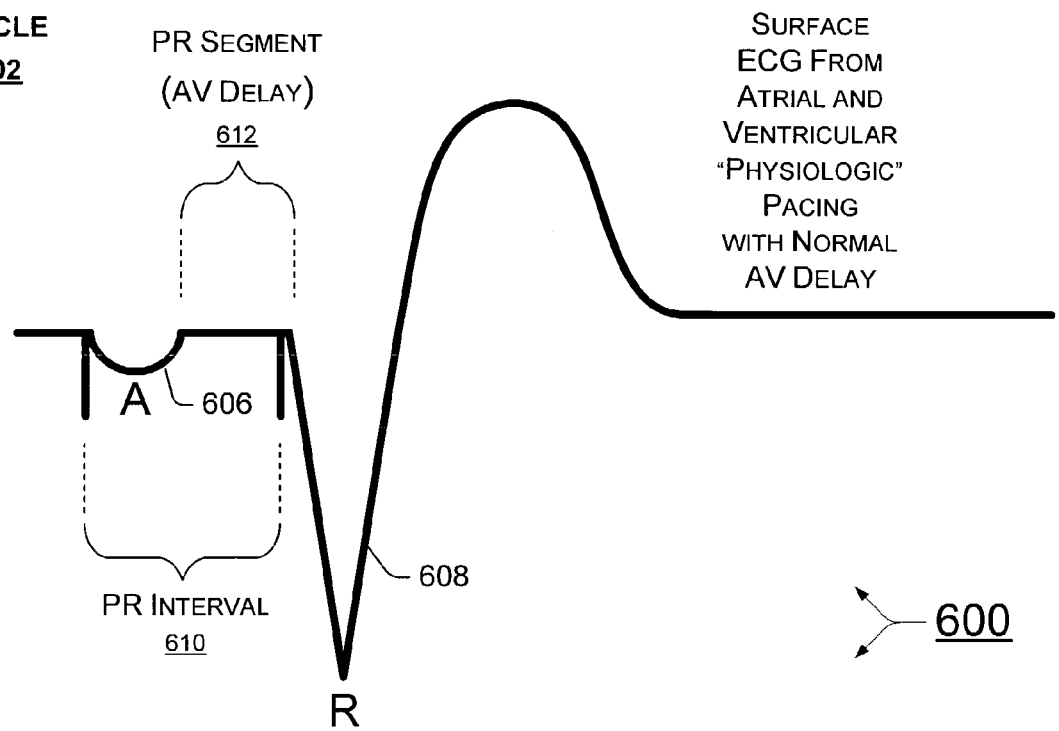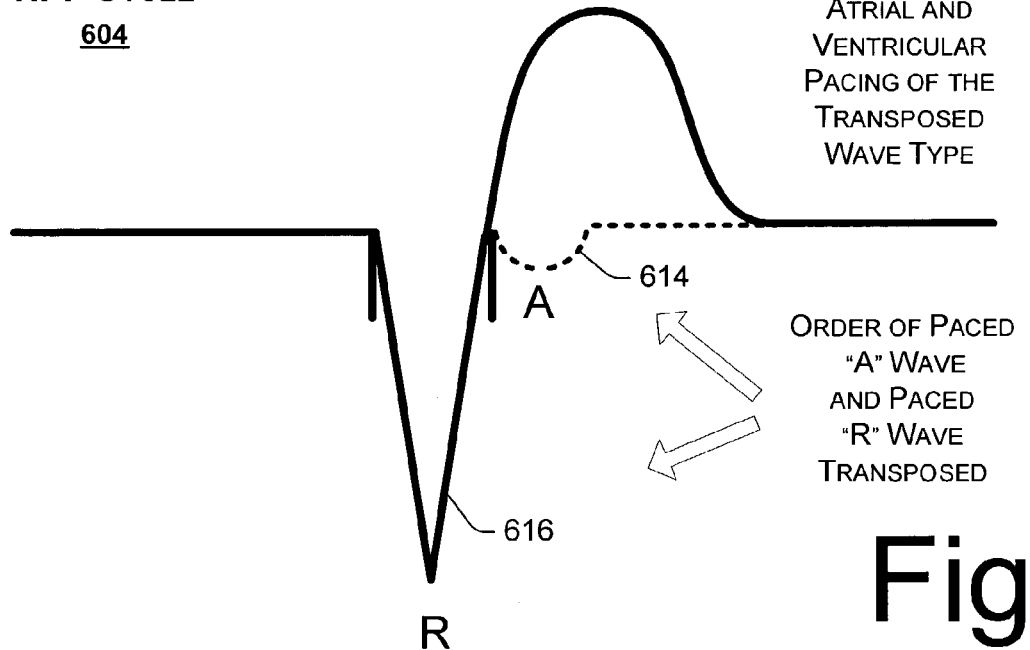
Fig.6

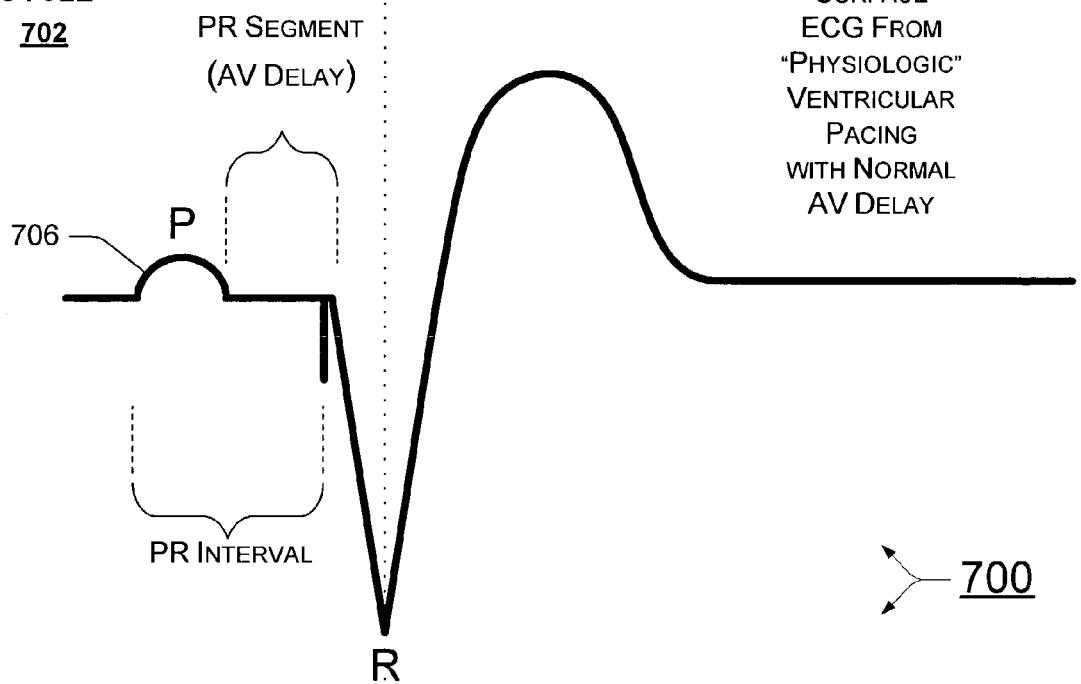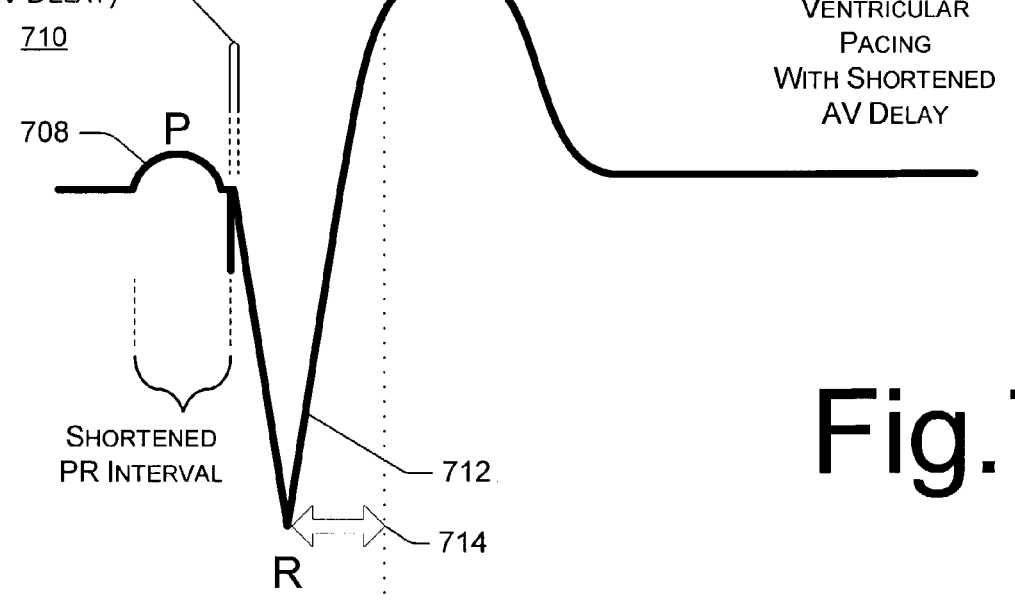
Fig. 7

SYSTEM AND METHOD OF CARDIAC PACING DURING SLEEP APNEA

TECHNICAL FIELD

The present invention generally relates to implantable cardiac devices, and particularly, to techniques for treating sleep apnea in patients receiving pacing therapy via an implantable cardiac device.

BACKGROUND

Sleep apnea is a serious malady ranking second only to insomnia as the most prevalent sleep disorder. Symptoms of sleep apnea include snoring, breath holding during sleep, rapid awakening with gasping for air, morning headaches, depression, irritability, loss of memory, lack of energy, and high risk of automobile and workplace accidents.

Apnea occurs when breathing difficulty causes the oxygenation of blood and body tissues to fall dangerously low. The brain often reacts by directing a release of adrenalin, which can arouse the apneic patient. Thereafter, regular breathing and normal exchange of oxygen and accumulated carbon dioxide resumes. Severe sleep apnea, however, may result in hundreds of episodes of oxygen desaturation during 6–8 hours of attempted sleep. The typical sleep apnea patient is not conscious of the struggle for oxygen, but may feel tired and ill in the morning.

Sleep apnea has multiple classifications based on the source of dysfunction. Obstructive sleep apnea results from mechanical blockage of the airway, for example, due to the weight of fatty neck tissue compressing the trachea. Central sleep apnea results from neurological dysfunction. Mixed sleep apnea has a combination of mechanical and neurological cause.

Sleep apnea can be life-threatening, especially when it occurs in conjunction with coronary artery disease (CAD) or congestive heart failure (CHF or "heart failure"). Not only does sleep apnea place a tremendous burden on the heart and the entire cardiopulmonary system directly, but it also circumvents the normal architecture of human sleep, which affects the heart indirectly. The apnea-induced alteration of the sleep cycle, including reduced slow-wave (deep) and REM (dream) segments, causes sleep to be ineffective. A vicious cycle follows as an unremitting sleep debt and daytime weariness worsen CAD, CHF, and hypertension. Consequently, sleep apneics who have a blood oxygen level lowered by sleep-disordered breathing are at an increased risk for hypertension, arrhythmias, heart attack, stroke, and nocturnal sudden death.

Approximately fifty percent of patients with heart failure suffer from sleep apnea. About ten percent of the heart failure patients suffer from obstructive sleep apnea, while about forty percent of patients with heart failure suffer from central sleep apnea. A high comorbidity exists between sleep apnea and certain types of CHF, which results from a negative synergy between the gas exchange problem due to mechanical breathing dysfunction during apnea and the oxygen distribution problem caused by weak pumping and fluid buildup characteristic of CHF. CHF is a condition in which a weakened heart cannot pump enough blood to body organs. Failing myocardium due to CHF may affect either the pumping action of the right side, left side, or both sides of the heart. The weak pumping action causes fluid to back up into other areas of the body including the liver, gastrointestinal tract, and extremities (right-sided heart failure), or the lungs (left-sided heart failure). Heart failure patients have characteristic pulmonary edema or pitting edema of the lower legs.

Sleep apnea may be treated by administering continuous positive airway pressure (CPAP) via a machine or by various other treatments, such as surgery and medications. The type of treatment depends on the type of sleep apnea. It is generally believed that reducing heart failure symptoms reduces the apnea burden, which in turn further reduces the heart failure symptoms. Cardiac pacing can also affect sleep apnea. There is a need to improve the techniques for applying pacing therapy from implantable cardiac devices in a manner that effectively combats sleep apnea.

SUMMARY

An exemplary method for treating sleep apnea includes determining a parameter for a cardiac pacing pulse where the cardiac pacing pulse aims to create a hemodynamic imbalance within the patient's cardiovascular system. The hemodynamic imbalance within the patient's cardiovascular system provokes a corrective or compensatory response, including a resumption in breathing. An exemplary implantable cardiac device is programmable to perform such an exemplary method. Other exemplary methods, devices, and/or media are also disclosed.

The parameters for a cardiac pacing pulse that aims to create a hemodynamic imbalance may include the length of the AV delay, the ordering and spacing of atrial and ventricular events in the cardiac cycle, etc. A cardiac pacing pulse that aims to cause a hemodynamic imbalance is called a "non-physiological" pacing pulse, or "NPP" pulse. In other words, an NPP pulse aims to alter the physiologic performance of the heart, typically in a manner that provokes the compensatory and/or corrective response to end the episode of sleep apnea.

An NPP pulse may result in a temporary undesirable condition. The hemodynamic imbalances created by NPP pulses, however, are sensed and transmitted by afferent nerve pathways to the central nervous system to provoke the cardiovascular and/or respiratory control centers to take corrective action. The corrective action may include taking an inventory of respiratory status, normalizing blood pressure, changing the sympathetic/parasympathetic tone of the heart, and restoring neural and hormonal balance through a resumption of breathing.

BRIEF DESCRIPTION OF THE DRAWINGS

FIG. 6 is a diagrammatic illustration showing a comparison between a physiologic pacing cycle and an exemplary second type of non-physiologic pacing cycle.

FIG. 7 is a diagrammatic illustration showing a comparison between a physiologic pacing cycle and an exemplary third type of non-physiologic pacing cycle.

DETAILED DESCRIPTION

Overview

In the following discussion, an exemplary technique is described for treating sleep apnea in patients receiving cardiac pacing therapy. An exemplary implantable cardiac device is programmable to perform the exemplary technique. Other exemplary methods, devices, and/or media are also disclosed.

In addition to providing the cardiac pacing therapy, an exemplary device can be programmed to perform the exemplary technique, detecting sleep apnea during rest mode pacing and delivering non-physiologic pacing ("NPP") to reduce sleep apnea. A non-physiologic pacing pulse ("NPP pulse") used in NPP is a pacing pulse that creates a hemodynamic imbalance, alerting the central nervous system to restore neural and hormonal balance, especially via a resumption of breathing. The restoration of breathing ultimately benefits the patient's heart making up for temporary electrical and hemodynamic imbalances caused by one or more NPP pulses. While application of NPP pulses might cause a mild startle response in an awake patient, NPP pulses applied in a sleeping patient aim to prod the central nervous system to resume or continue normal respiration without waking the patient.

NPP therapy consists of substituting a NPP pulse or sets of NPP pulses during sleep. NPP therapy can also be modified during application by changing the morphology of individual cardiac cycles during which NPP pulses are applied. The number of NPP pulses in each set to be applied can also be modified, and the duration of the interval of baseline rest mode pacing that is applied between each NPP set can be modified. The modifications can be based on feedback received by an exemplary device.

An implantable cardiac device 100 is commonly characterized as a miniature computer that is implanted into the body of a patient to monitor, regulate, and/or correct cardiac and other activity. Such devices include implantable cardiac stimulation devices (e.g., implantable cardiac pacemakers, implantable defibrillators) that apply stimulation therapy to the heart. The following discussion describes first an exemplary cardiac device that is effective for treating cardiac conditions, such as those related to heart failure, and then a describes a mode of operation in which sleep apnea episodes are detected and NPP therapy is applied to alleviate the episodes.

Exemplary Implantable Cardiac Device

Figure 1:
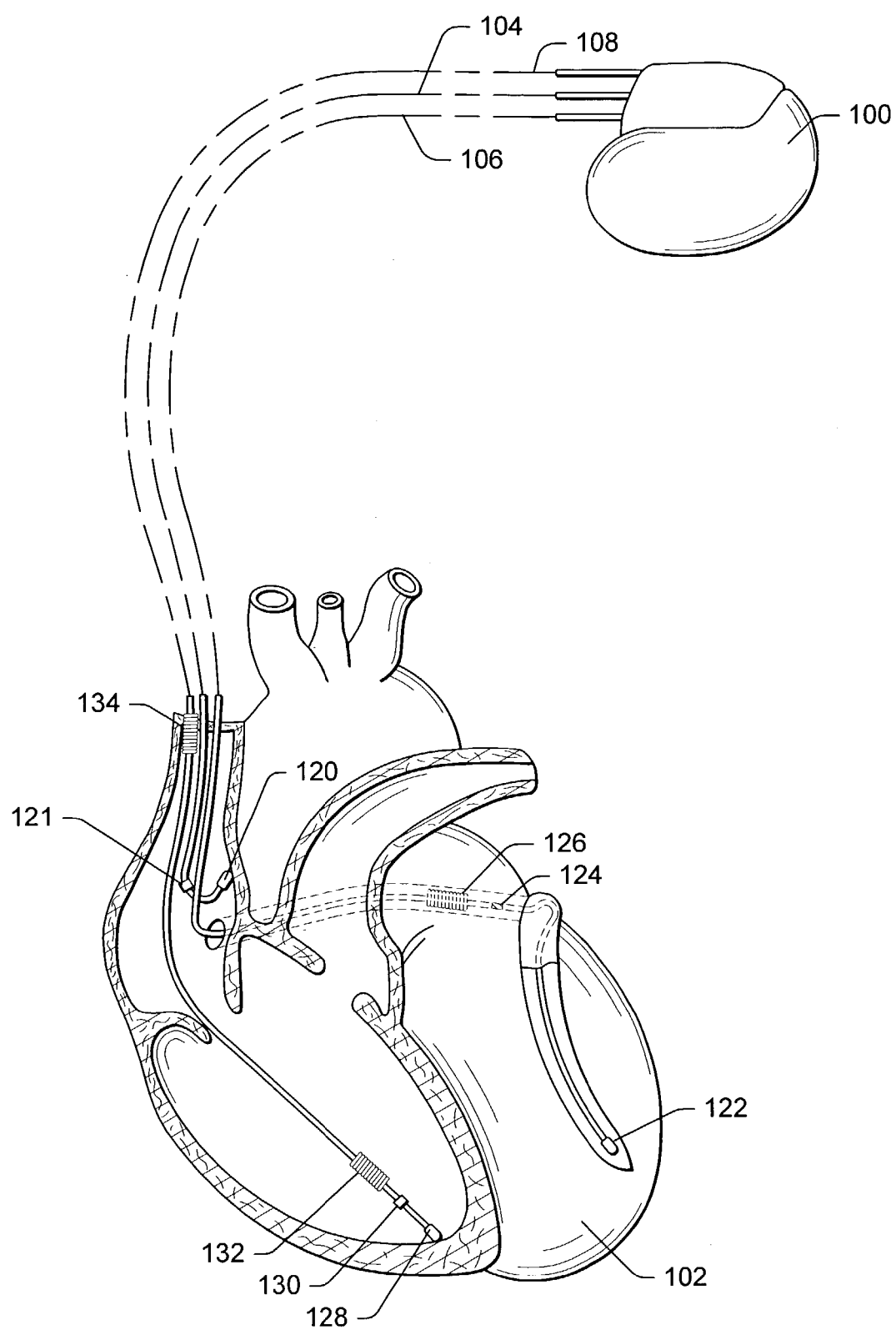
FIG. 1 is a diagrammatic illustration of an implantable cardiac device in electrical communication with a patient's heart for multi-chamber sensing and delivery of multi-chamber stimulation, as well as application of non-physiologic pacing therapy to treat sleep apnea.

FIG. 1 shows an exemplary implantable cardiac device 100 in electrical communication with a patient's heart 102 for monitoring heart activity and/or delivering stimulation therapy, such as pacing therapies and NPP therapy. Three leads—a right atrial lead 104, a coronary sinus lead 106, and a right ventricular lead 108—interconnect the device 100 with the patient's heart 102 to support multi-chamber detection and stimulation therapy.

The right atrial lead 104 supports an atrial tip electrode 120, which typically is implanted in the patient's right atrial appendage. The right atrial lead 104 also supports a right atrial ring electrode 121, which enables the device to sense atrial cardiac signals and apply pacing therapy to the right atrial chamber.

The coronary sinus lead 106 positions a left ventricular tip electrode 122 adjacent to the left ventricle and/or additional electrode(s) adjacent to the left atrium, such as a left atrial ring electrode 124 and a left atrial coil electrode 126. The coronary sinus lead 106 enables the device 100 to sense left atrial and ventricular cardiac signals and administer left chamber pacing therapy. In the illustrated arrangement, the left ventricular tip electrode 122 is used to sense atrial and ventricular cardiac signals and deliver left ventricular pacing therapy. The left atrial ring electrode 124 is employed for applying left atrial pacing therapy, and the left atrial coil electrode 126 is used for shocking therapy.

The right ventricular lead 108 is electrically coupled to a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of receiving cardiac signals, and delivering stimulation in the form of pacing and shock therapy to the right ventricle.

Figure 2:
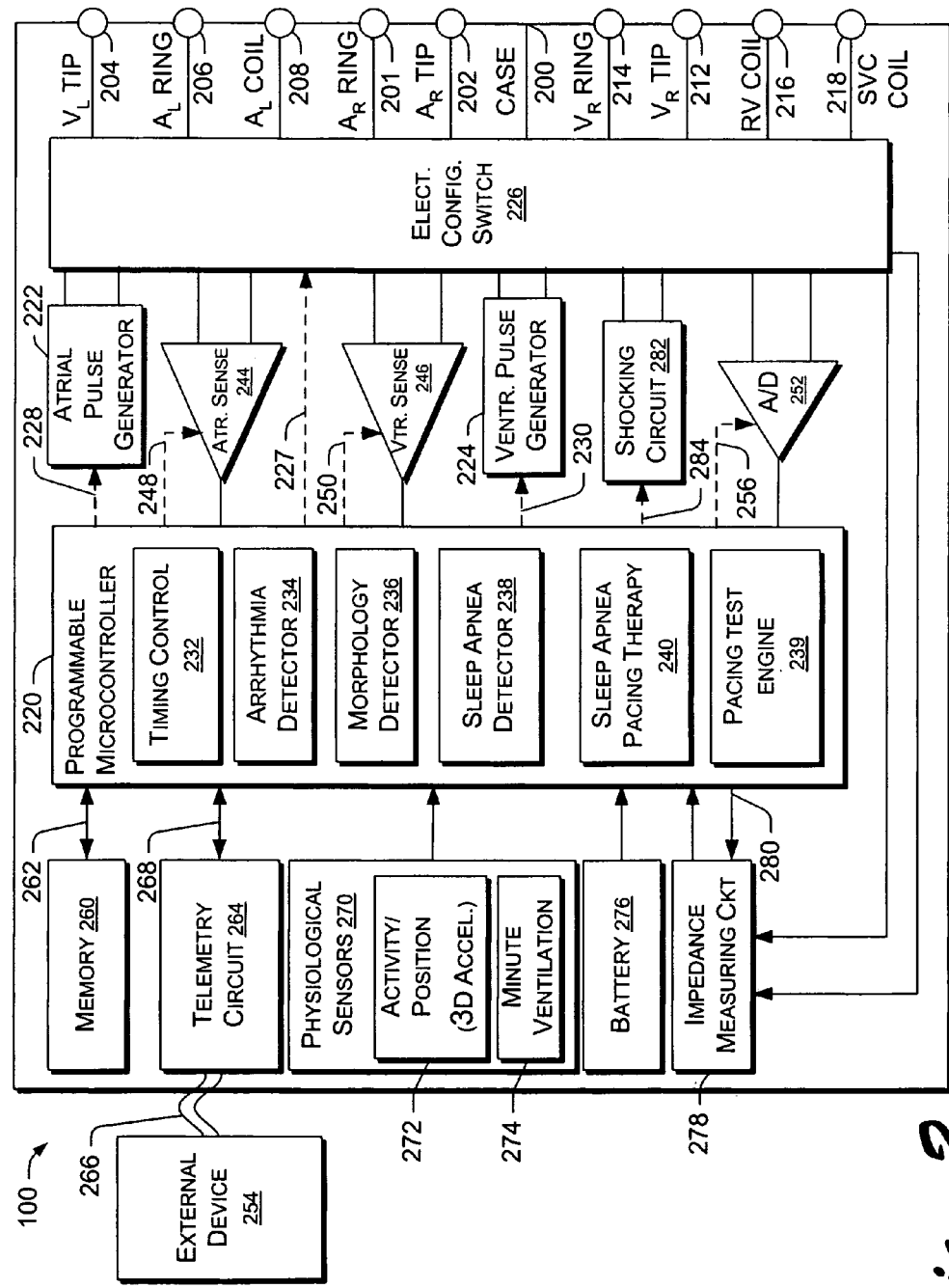
FIG. 2 is a functional block diagram of the multi-chamber implantable cardiac device.

FIG. 2 shows an exemplary, simplified block diagram depicting various components of the implantable cardiac device 100. The components are housed in housing 200, which is often referred to as the "can", "case", "encasing", or "case electrode", and may be programmably selected to act as the return electrode for unipolar modes. Housing 200 may further be used as a return electrode alone or in combination with one or more of the coil electrodes 126, 132 and 134 for stimulating purposes. Housing 200 further includes a connector (not shown) having a plurality of terminals 202, 204, 206, 208, 212, 214, 216, and 218 (shown schematically and, for convenience, the names of the electrodes to which they are connected are shown next to the terminals), including:

- a right atrial ring terminal ($A_R$ RING) 201 for atrial ring electrode 121;
- a right atrial tip terminal ($A_R$ TIP) 202 for atrial tip electrode 120;
- a left ventricular tip terminal ($V_L$ TIP) 204 for left ventricular tip electrode 122;
- a left atrial ring terminal ($A_L$ RING) 206 for left atrial ring electrode 124;
- a left atrial shocking terminal ($A_L$ COIL) 208 for left atrial coil electrode 126;
- a right ventricular tip terminal ($V_R$ TIP) 212 for right ventricular tip electrode 128;
- a right ventricular ring terminal ($V_R$ RING) 214 for right ventricular ring electrode 130;
- a right ventricular shocking terminal (RV COIL) 216 for RV coil electrode 132; and
- an SVC shocking terminal (SVC COIL) 218 for SVC coil electrode 134.

The implantable cardiac device 100 includes a programmable microcontroller 220 that controls various operations of the implantable cardiac device, including cardiac monitoring and stimulation therapy. Microcontroller 220 includes a microprocessor (or equivalent control circuitry), RAM and/or ROM memory, logic and timing circuitry, state machine circuitry, and I/O circuitry.

Device 100 further includes an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. The switch 226 includes multiple switches for connecting the desired electrodes to the appropriate I/O circuits, thereby providing complete electrode programmability. Accordingly, switch 226, in response to a control signal 227 from the microcontroller 220, determines the polarity of the stimulation pulses (e.g., unipolar, bipolar, etc.) by selectively closing the appropriate combination of switches.

To provide stimulation therapy in each of the four chambers of the heart, the atrial and ventricular pulse generators 222 and 224 may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 is illustrated as including timing control circuitry 232 to control the timing of the stimulation pulses (e.g., pacing rate, atrioventricular (AV) delay, atrial interconduction (A—A) delay, or ventricular interconduction (V—V) delay, native atrial event to native or stimulated ventricular event (PV) delay, (AV/PV) delay, etc.). The timing control circuitry may also be used for the timing of refractory periods, blanking intervals, noise detection windows, evoked response windows, alert intervals, marker channel timing, and so on.

Microcontroller 220 is also equipped with an arrhythmia detector 234, a morphology detector 236, a sleep apnea detector 238, a pacing test engine 239, and a sleep apnea pacing therapy module 240. The sleep apnea detector 238 is configured to detect episodes of sleep apnea. In some implementations, the sleep apnea detector 238 may also be programmed to anticipate onset of sleep apnea, which can facilitate measurement of sleep apnea. One approach for detecting sleep apnea is via direct measurement of a parameter suggestive of apnea. For instance, the detector might detect changes in respiration, heart rate, abdominal movement, leg jerking, and/or minute ventilation as being suggestive of sleep apnea. Another approach is for the sleep apnea detector 238 to detect coinciding changes of two or more parameters that indicate onset of sleep apnea. For instance, an exemplary detector may anticipate an upcoming sleep apnea episode if the patient, while resting, experiences a decrease in minute ventilation and a concurrent drop in heart rate. In another approach, the sleep apnea detector 238 uses pattern analysis to anticipate sleep apnea. The detector compares current physiological parameters with patterns of the same parameters captured during previous sleep apnea episodes to determine whether the current parameters suggest onset of sleep apnea.

In one implementation, the sleep apnea pacing therapy module 240 delivers NPP therapy to treat sleep apnea. This module is optionally used to implement various exemplary methods presented below, such as those described with reference to FIGS. 3–10.

Each of the components 234–240 may be implemented in hardware as part of the microcontroller 220, or as software/firmware instructions programmed into the device and executed on the microcontroller 220 during certain modes of operation. Although not shown, the microcontroller 220 may further include other dedicated circuitry and/or firmware/software components that assist in monitoring various conditions of the patient's heart and managing pacing therapies.

Atrial sensing circuits 244 and ventricular sensing circuits 246 may also be selectively coupled to the right atrial lead 104, coronary sinus lead 106, and the right ventricular lead 108, through the switch 226 to detect the presence of cardiac activity in each of the four chambers of the heart. The sensing circuits 244 and 246 may include dedicated sense amplifiers, multiplexed amplifiers, or shared amplifiers. Switch 226 determines the "sensing polarity" of the cardiac signal by selectively closing the appropriate switches. In this way, the clinician may program the sensing polarity independent of the stimulation polarity.

Each sensing circuit 244 and 246 may employ one or more low power, precision amplifiers with programmable gain and/or automatic gain control, bandpass filtering, and threshold detection circuit to selectively sense the cardiac signal of interest. The automatic gain control enables the device 100 to sense low amplitude signal characteristics of atrial or ventricular fibrillation.

The outputs of the atrial and ventricular sensing circuits 244 and 246 are connected to the microcontroller 220 which, in turn, is able to trigger or inhibit the atrial and ventricular pulse generators 222 and 224 in a demand fashion in response to the absence or presence of cardiac activity in the appropriate chambers of the heart. The sensing circuits 244 and 246 receive control signals from the microcontroller 220 over signal lines 248 and 250 for purposes of controlling the gain, threshold, polarization charge removal circuitry (not shown), and the timing of any blocking circuitry (not shown) coupled to the inputs of the sensing circuits.

Cardiac signals are supplied to an analog-to-digital (A/D) data acquisition system 252, which is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, and the right ventricular lead 108 through the switch 226 to sample cardiac signals across any pair of desired electrodes.

The data acquisition system 252 is coupled to the microcontroller 220, or other detection circuitry, to assist in detecting an evoked response from the heart 102 in response to an applied stimulus, which is otherwise known as detecting "capture". Capture occurs when an electrical stimulus applied to the heart is of sufficient energy to depolarize the cardiac tissue, thereby causing the heart muscle to contract. The microcontroller 220 detects a depolarization signal during a window following a stimulation pulse, the presence of which indicates that capture has occurred. The microcontroller 220 enables capture detection by triggering the ventricular pulse generator 224 to generate a stimulation pulse, starting a capture detection window using the timing control circuitry 232 within the microcontroller 220, and enabling the data acquisition system 252 via control signal 256 to sample the cardiac signal that falls in the capture detection window and, based on the amplitude, determines if capture has occurred.

The microcontroller 220 is further coupled to a memory 260 by a suitable data/address bus 262. The programmable operating parameters used by the microcontroller 220 are stored in memory 260 and used to customize the operation of the device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy.

The operating parameters of the implantable device 100 may be non-invasively programmed into the memory 260 through a telemetry circuit 264 in telemetric communication via communication link 266 with the external device 254, such as a programmer, local transceiver, or a diagnostic system analyzer. The microcontroller 220 activates the telemetry circuit 264 with a control signal 268. The telemetry circuit 264 allows intracardiac electrograms and status information relating to the operation of the device 100 (as contained in the microcontroller 220 or memory 260) to be sent to the external device 254 through an established communication link 266.

The implantable cardiac device 100 can further include one or more physiologic sensors 270. Such sensors are commonly referred to as "rate-responsive" sensors because they are typically used to adjust pacing stimulation rates according to the exercise state of the patient. However, the physiological sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V—V Delay, etc.) at which the atrial and ventricular pulse generators 222 and 224 generate stimulation pulses. While shown as being included within the device 100, the physiologic sensor(s) 270 may also be external to the device 100, yet still be implanted within or carried by the patient.

Two examples of physiological sensors are shown: an activity/position sensor 272 (e.g., 3D accelerometer, activity sensor, etc.) to detect movement in the patient's position and a minute ventilation (MV) sensor 274 to sense minute ventilation. Minute ventilation is the total volume of air that moves in and out of a patient's lungs in a minute. The MV sensor 274 uses transthoracic impedance, which is a measure of impedance across the chest cavity, to sense air movement. Lungs filled with air have higher impedance than empty lungs. Thus, upon inhalation, impedance increases and upon exhalation, impedance decreases. Other examples of physiologic sensors might include sensors that, for example, sense respiration rate, pH of blood, ventricular gradient, and so forth.

Signals generated by the physiological sensors are passed to the microcontroller 220 for analysis by the sleep apnea detector 238. Such signals can be used to determine whether the patient is at rest, whether the patient is experiencing an episode of sleep apnea, and whether to invoke any responsive therapy prescribed by the pacing therapy module 240.

The implantable cardiac device 100 additionally includes a battery 276 that provides operating power to all of the components shown in FIG. 2. The battery 276 is capable of operating at low current drains for long periods of time (e.g., less than 10 µA), and is capable of providing high-current pulses (for capacitor charging) when the patient requires a shock pulse (e.g., in excess of 2 A, at voltages above 2 V, for periods of 10 seconds or more). The battery 276 also desirably has a predictable discharge characteristic so that elective replacement time can be detected. As one example, the device 100 employs lithium/silver vanadium oxide batteries.

The device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The device 100 further includes an impedance measuring circuit 278 that is enabled by the microcontroller 220 via a control signal 280. The impedance measuring circuit 278 is used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 278 is coupled to the switch 226 so that any desired electrode may be used.

The device 100 can be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 joules), moderate (e.g., 0.5–10 joules), or high energy (e.g., 11 to 40 joules), as controlled by the microcontroller 220. Such shocking pulses are applied to the patient's heart 102 through at least two shocking electrodes selected, for example, from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of, e.g., 5–40 joules), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

The implantable cardiac device 100 can be programmed to treat both heart failure and sleep apnea using pacing therapy. To treat heart failure, the device delivers pacing pulses of a voltage level via a lead in the left-sided veins.

More generally, the device 100 can be programmed to stimulate different sets of muscles through the same lead/electrode system. The device 100 can be programmed to vary the output voltage of various pulses to effectively stimulate different muscles of the heart, even though the lead and electrode placement does not change.

Non-physiologic Sleep Apnea Pacing Therapy

NPP therapy to treat sleep apnea includes an exemplary method for determining parameters for a cardiac pacing pulse based, at least in part, on information characteristic of sleep apnea, wherein the cardiac pacing pulse aims to create a hemodynamic imbalance, i.e., the cardiac pacing pulse is a non-physiologic (NPP) pulse. As described above, such a NPP pulse aims to provoke a corrective and/or compensatory response to a temporarily undesirable hemodynamic condition. A device programmed to apply NPP therapy, such as the exemplary device 100, can monitor the hemodynamic imbalances created by NPP pulses to ensure safe NPP therapy.

Figure 3:
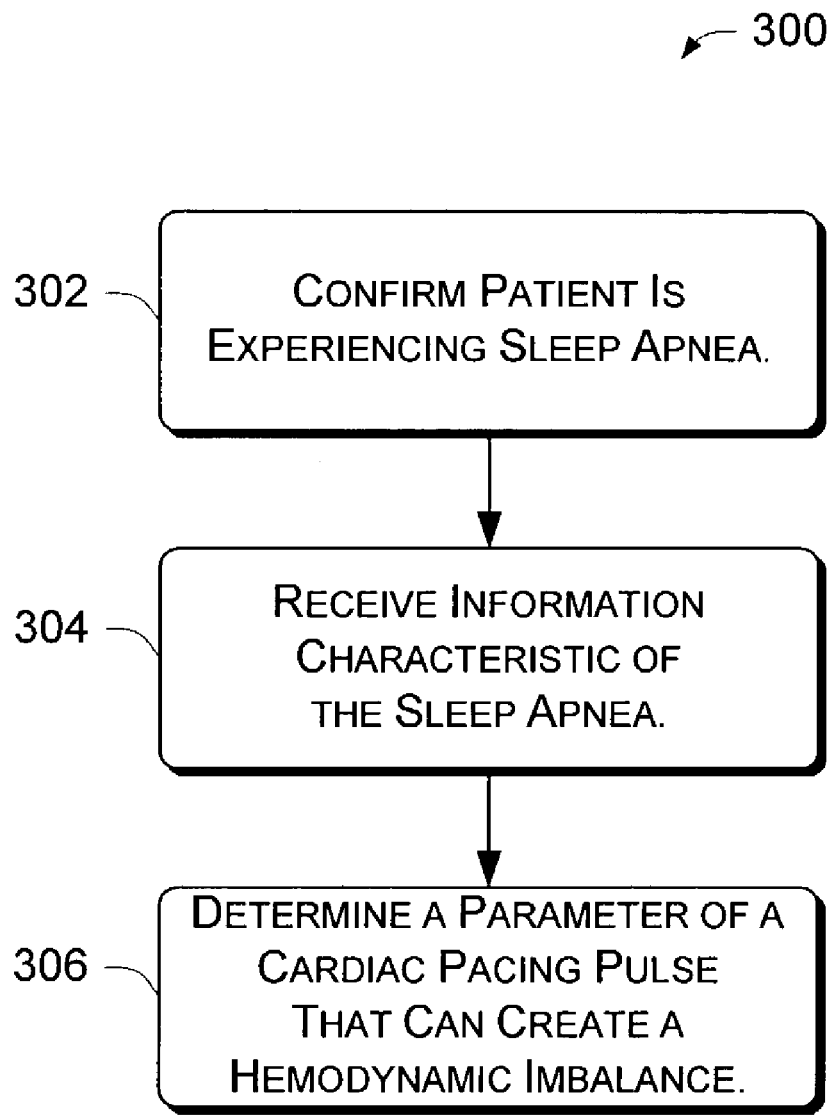
FIG. 3 is a flow diagram of an exemplary method for treating sleep apnea.

FIG. 3 shows an exemplary method 300 for performing sleep apnea therapy during cardiac pacing therapy. According to this exemplary method 300, a suitable implantable cardiac device (e.g., the exemplary implantable cardiac device 100, etc.) is programmed to apply cardiac pacing pulses and to apply NPP therapy to treat episodes of sleep apnea. Although this process 300 is described as being executed by the exemplary implantable cardiac device 100 of FIGS. 1 and 2, of course other suitable devices may be used to implement the exemplary process 300. In the flow diagram, the operations are summarized in individual blocks. The operations may be performed in hardware and/or as machine-readable instructions (software or firmware) that can be executed by a processor.

At block 302, confirmation is made that the patient is experiencing sleep apnea. The confirmation may optionally be made by the exemplary sleep apnea detector 238, or in other implantable devices by hardware and/or software that can sense sleep apnea. Alternatively, the confirmation of sleep apnea in block 302 is skipped, but information characteristic of sleep apnea may be sensed for the reception in block 304.

At block 304, if the patient is experiencing sleep apnea, then information characteristic of the sleep apnea is received. An implantable device, such as exemplary device 100 may be programmed to sense and/or to receive the information. Information may include timekeeping and/or physiological reading, such as the starting time or likely onset time of a sleep apnea episode, duration and severity of the sleep apnea episode, heart rate, blood gas and pH levels, bodily movements, history of response to sleep apnea therapy, etc.

At block 306, a parameter of a cardiac pulse that can be used to create a hemodynamic imbalance, i.e., an NPP pulse, is determined based on the sleep apnea information. Parameters to be determined at block 306 can include not only parameters of a NPP pulse, but also parameters of the NPP therapy context in which a NPP pulse is used. Example parameters can include amplitude of the NPP pulse, morphology of the cardiac electrical cycle that includes or is comprised of the NPP pulse(s), application patterns for delivering repetitive NPP pulses, lengths of NPP pulse sets, intervals between sets, plans to modify NPP therapy based on feedback, etc.

In one implementation, a programmed device, such as the exemplary device 100, delivers a NPP therapy by periodically substituting NPP pulses for regular rest mode pacing pulses in a rest mode pacing regimen. An NPP set usually includes approximately 1 to approximately 20 NPP pulses. Each NPP pulse may initiate a temporary dysrhythmia lasting one heartbeat that jars the cardiovascular and/or respiratory control centers in the central nervous system by upsetting normal hemodynamic flow in the heart and nearby great vessels. A description of how NPP pulses may provoke the central nervous system in the treatment of sleep apnea follows.

Physiological Effects of Non-physiologic Pacing Therapy

The manner in which NPP therapy alerts the cardiovascular and/or respiratory control centers in the central nervous system to resume normal breathing is complex, however, the following explanation is provided.

If an exemplary NPP pulse is of a type that causes an extrasystole or other ventricular anomaly in the ventricular filling and/or ejection segments of the cardiac cycle then a sudden backpressure wave can be created in the atria, the superior vena cava, the inferior vena cava, and the pulmonary veins as the contraction of the ventricles closes the atrioventricular valves at an abnormal time against contracting atria. The same backpressure wave may occur in the aorta and pulmonary arteries depending on the precise point in the cardiac cycle where the PVC or extrasystole occurs. The backpressure wave may be followed by rebound low pressure waves. The pressure waves and their effects are sensed by baroreceptors and other sensors.

Arterial baroreceptors, which constitute an essential sensory link to the brain stem for the short-term regulation of blood pressure, are thought to also influence higher cortical function. The baroreceptors are stretchable mechanoreceptors on the elastic walls of the great vessels that can sense the altered hemodynamics caused by an applied NPP pulse and send afferent impulses to the control centers in the brain stem. The goal of applying NPP pulses is to send enough afferent stimulation (indicating a disturbance) to the brain stem to prod the central nervous system into taking notice and sending efferent correctives (improved sympathetic/parasympathetic tone at the heart and lungs, resumption of breathing, etc.) without waking up the patient.

Any change in mean blood pressure following application of a NPP pulse triggers an autonomically mediated baroreceptor reflex that influences the heart and blood vessels to adjust cardiac output and total peripheral resistance in an attempt to restore blood pressure to normal. Like any reflex, the baroreceptor reflex involves a receptor, an afferent pathway, an integrating center, i.e., the cardiovascular control center, an efferent pathway (e.g., the sympathetic and parasympathetic branches of the autonomic nervous system), and effector organs. The most important baroreceptors involved in moment-to-moment regulation of blood pressure, the carotid-sinus and aortic-arch baroreceptors, are sensitive to changes both in mean arterial pressure and in pulse pressure. Their responsiveness to fluctuations in pulse pressure enhances their sensitivity as pressure sensors, because small changes in systolic or diastolic pressure may alter the pulse pressure without changing the mean pressure. These baroreceptors are strategically located to provide critical information about arterial blood pressure in the vessels leading to the brain (the carotid-sinus baroreceptor) and in the major arterial trunk before branching off to supply the rest of the body (the aortic-arch baroreceptor).

The above-mentioned integrating center that receives the afferent impulses regarding the status of arterial pressure, i.e., the cardiovascular control center, is located in the medulla portion of the brain stem. If the efferent pathway is the autonomic nervous system the cardiovascular control center can alter the ratio of sympathetic to parasympathetic activity to the heart and blood vessel effector organs to maintain blood pressure homeostasis.

When blood pressure falls below normal, even for a split second, the baroreceptors decrease the rate of firing in their afferent neurons, inducing the cardiovascular control center to decrease its parasympathetic output while increasing sympathetic cardiac and vasoconstrictor nerve activity. This efferent pattern of activity leads to an increase in heart rate and stroke volume coupled with arteriolar and venous vasoconstriction. These changes result in an increase in both cardiac output and total peripheral resistance, producing an elevation in blood pressure back toward normal. These cardiovascular changes may provide a cue to the respiratory control center to resume breathing, thereby ending the episode of sleep apnea.

When a NPP pulse is applied, many other types of receptors besides baroreceptors may initiate a signal to the brain stem warning of an imbalance. Chemoreceptors located in the carotid and aortic arteries, in close association with but distinct from the baroreceptors, are sensitive to low oxygen or high acid levels in the blood. The main function of these chemoreceptors is to increase respiratory activity to inhale more oxygen or to exhale more acid-forming carbon dioxide, but they also increase blood pressure by sending excitatory impulses to the cardiovascular center. If the applied NPP pulses cause incomplete filling of the ventricles, then the cardiac output may be ineffective and a low systolic blood pressure, poor ejection, and/or no pumping period may trigger these chemoreceptors since they detect tiny changes in the partial pressure of carbon dioxide in the arterial blood gases.

For driving respiration, the detection of carbon dioxide partial pressure is the most important afferent input to the medullary respiratory center of the brain stem, having the greatest effect in regulating the magnitude of ventilation under resting conditions. The effects of applied NPP pulses may stimulate chemoreceptors that have lost some of their sensitivity to carbon dioxide so that the chemoreceptors notify the brain stem that the partial pressure of carbon dioxide in the blood is too high, causing the brain stem to modify the blood's bicarbonate system—by resuming breathing—to lower the carbon dioxide.

Furthermore, application of NPP therapy may stimulate the balance of various hormones and peptides relevant to sleep apnea and cardiac pathologies such as CHF. The sensing of a hemodynamic imbalance caused by a NPP-induced "skipped-beat" or "extra beat" may elicit a sympathetic stimulus that results in the central nervous system triggering the mild release of a catecholamine of the adrenaline type.

Moreover, pulmonary edema and edema of the extremities are common effects of CHF suffered concurrently with sleep apnea. Release of naturetic peptides is beneficial to these edematous states since the peptides reverse salt and water retention and cause vasodilation which counteracts the constriction of vessels that occurs with angiotensin-aldosterone activation. Since a predominant location for the production of one of the primary peptides, beta naturetic peptide (BNP), is the ventricles, increases in the tension and stretch of the ventricle walls stimulates a higher blood concentration of BNP. It is thought that BNP is synthesized in bursts, thus levels of BNP may change rapidly depending on the patient's instantaneous hemodynamic balance or imbalance. Thus, when NPP therapy is applied, resulting hemodynamic imbalances may stimulate the production of beneficial BNP likely to decrease sleep apnea.

Another group of receptors known as left atrial volume receptors respond to increases in transmural pressure: e.g., from increased left atrial volume. Impulses transmitted to the osmoregulatory centers of the hypothalamus result in reduced ADH (antidiuretic hormone, vasopressin) secretion thereby increasing body water loss. Reflex hypotension and bradycardia sometimes follow left atrial distention.

Receptors can also cause hormone secretion. For example, mammalian atria have secretory granules containing another peptide, atrial naturetic peptide (ANP). ANP is secreted on stretch of the atria. This potent, short lived peptide induces renal secretion of sodium and increase diuresis thus serving to decrease plasma volume. ANP appears to decrease cardiac output by decreasing systemic resistance and by increase capillary filtration.

Ventricular responses, mostly in the left ventricle, include the Bezold-Jarish Reflex, which results from ventricular wall distention stimulating ventricular mechanoreceptors. Such receptors appear to be active only in extreme conditions to protect the ventricle from volume overload (they elicit hypotension and bradycardia). The response is a reflex vagal slowing of the heart and simultaneous inhibition of sympathoadrenal activity. The reflex protects against cardiac overstrain, pulmonary edema, and hypovolemia whenever cardiac distention is excessive (e.g., in some CHF patients). The reflex, transmitted by afferent vagal fibers, is thought to exert its sympathetic block via release of endogenous opiods likely acting on the delta-type opiod receptors in the brain.

In summary, during an episode of sleep apnea, the patient's respiratory and cardiovascular homeostasis is unbalanced. A hemodynamic imbalance resulting from application of NPP pulses can initiate numerous neural and hormonal reactions. Some of the neural and hormonal reactions initiated by NPP therapy may have an immediate balancing effect on the patient's disrupted homeostatis while other neural and hormonal reactions may serve to prod the respiratory centers of the brain into initiating a respiration cycle, ending the sleep apnea episode.

Non-physiologic Sleep Apnea Pacing Therapy with Feedback

Figure 4:
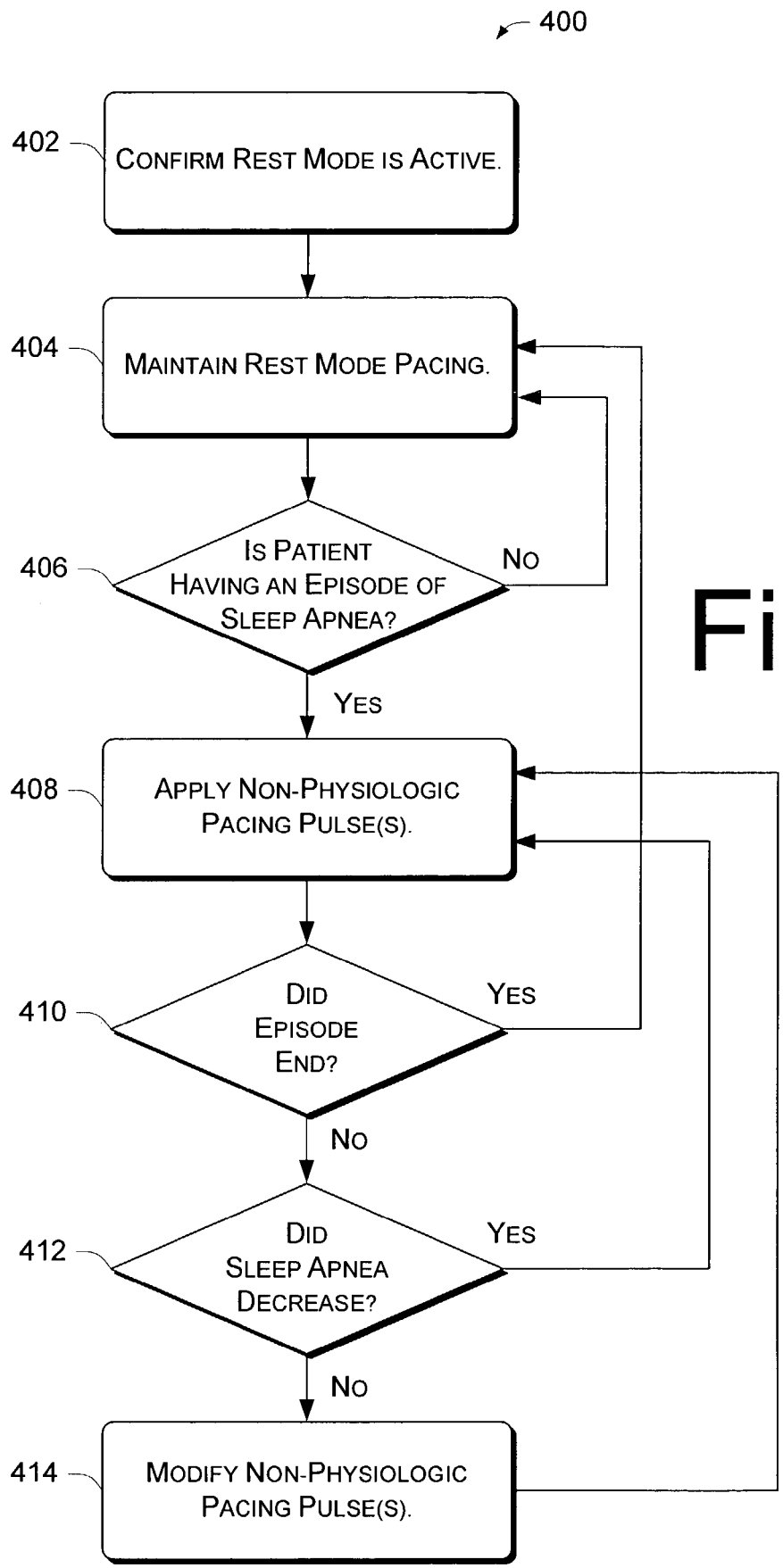
FIG. 4 is a flow diagram of an exemplary method for delivering non-physiologic sleep apnea pacing therapy, based on feedback.

FIG. 4 shows another exemplary method 400 for performing sleep apnea therapy during cardiac pacing therapy. According to this method 400, an implantable device, such as the exemplary device 100, is programmed to apply both cardiac pacing and NPP therapy for episodes of sleep apnea. Although this exemplary method 400 is described as being executed by the implantable cardiac device 100 of FIGS. 1 and 2, other devices may be used as well. In the flow diagram, the operations are summarized in individual blocks. The operations may be performed in hardware and/or as machine-readable instructions (software or firmware) that can be executed by a processor.

At block 402, confirmation is made that the patient is at rest, that is, rest mode is identified. If the patient is not at rest, then rest mode pacing is not active, and cessations in breathing detected by the device 100 may be due to voluntary breathholding by the patient.

At block 404, rest mode is maintained. Rest mode pacing typically uses a pacing rate that is 10–15% slower than the pacing rate in effect when the patient is awake, however, in patients with sleep apnea this rate may be elevated in relationship to the base rate. NPP therapy is generally applied when rest mode is active indicating the patient is in or approaching a sleep state.

At block 406, occurrence of an episode of sleep apnea is determined. As discussed above with reference to the exemplary microcontroller 220 in FIG. 2, an exemplary sleep apnea sensor, such as exemplary detector 238, may be configured to detect episodes of sleep apnea and, in some implementations, may be programmed to anticipate the onset of sleep apnea. If a device such as the exemplary sleep apnea detector 238 determines that the patient is not having an episode of sleep apnea, then the exemplary method 400 loops back to rest mode pacing, at block 404.

At block 408, if it has been determined that the patient is having an episode of sleep apnea, then NPP is applied. In this exemplary method 400, an exemplary device 100 can monitor the sleep apnea and adjust the NPP therapy depending on how the therapy is affecting the sleep apnea. At block 410, a device, such as exemplary device 100, determines whether the sleep apnea has ended. If the episode has ended, the exemplary device 100 may resume rest mode pacing with no added NPP therapy, looping back to block 404. If the exemplary device 100 determines that the episode did not end, then the exemplary device 100 further determines if the sleep apnea occurring within the episode has decreased 412. If the sleep apnea decreased during application of the NPP therapy, then NPP therapy may continue, as in block 408, and the sleep apnea may be monitored for further improvement.

In block 414, if the episode of sleep apnea did not end, and the sleep apnea did not decrease, the exemplary device 100 modifies the NPP therapy and applies the modified therapy, at block 408. There are a number of NPP therapy parameters that can be modified to find a therapy that ends or improves sleep apnea, as discussed above in relation to block 306 of FIG. 3. Non-physiologic Pacing Cycle Profiles A pacing cycle profile ("pacing profile") is a diagrammatic representation of a cardiac electrical cycle ("cycle"). A one heartbeat electrocardiogram (ECG) strip is one example of a pacing profile.

Figure 5:
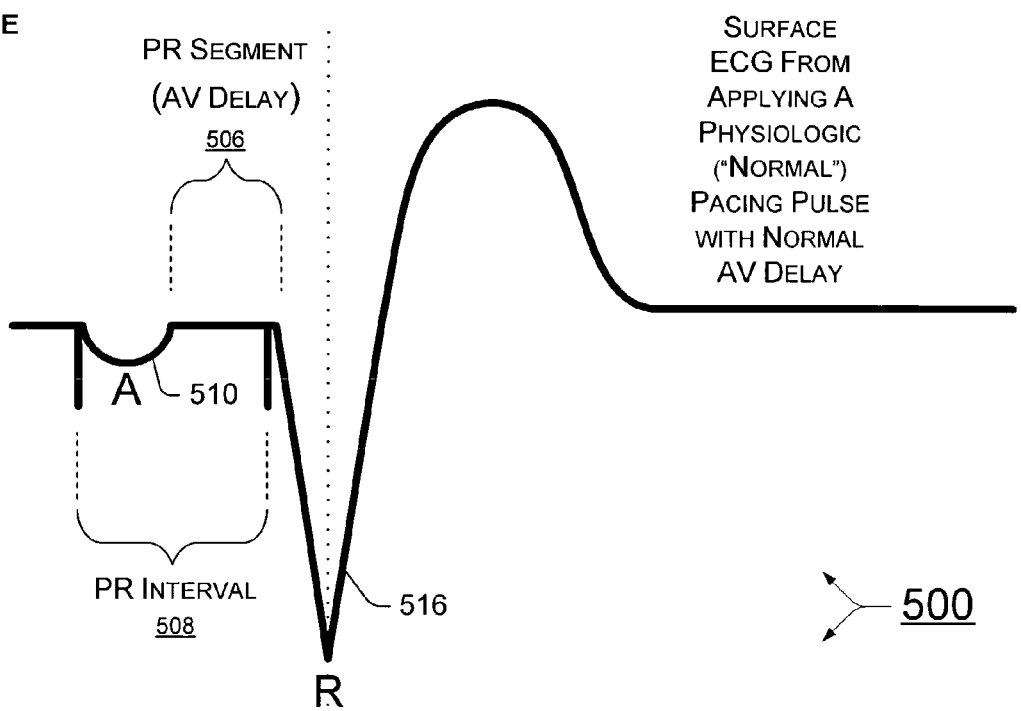
FIG. 5 is a diagrammatic illustration showing a comparison between a physiologic pacing cycle and an exemplary first type of non-physiologic pacing cycle.

FIG. 5 shows an exemplary comparison 500 of two A–V pacing profiles: a surface ECG representing the application of a physiologic cycle 502 (i.e., a normal rest mode pacing cycle described above with regard to block 304 of FIG. 3) and a surface ECG representing the application of an exemplary NPP cycle 504. It should be noted that the two pacing profiles are stylized for descriptive purposes, actual ECGs may vary from those shown in FIG. 5.

There are many parameters in the pacing profile of the physiologic cycle 502 that can be varied to create the NPP cycle 504. In the illustrated comparison 500, only one parameter, the atrioventricular delay (AV delay), has been varied. In dual-chamber pacing, the AV delay is the length of time (usually programmable) between an atrial sensed or atrial paced event and the delivery of a ventricular output pulse. The AV delay present in a healthy cardiac rhythm has been shortened by the device 100 to yield the ECG of the shown NPP cycle 504.

The AV delay is represented in the ECG of the physiologic cycle 502 by the PR segment 506 (the PR interval 508 minus the A wave 510). The PR interval 508 is a measure of the time from when the atria begin to pump blood into the ventricles to when the ventricles begin ejection. The AV delay (PR segment 506) represents an isoelectric interval during which no electrical current is flowing in the heart (except in the AV node), between the end of atrial contraction and the beginning of ventricular contraction. Whereas a normal AV delay is 140–200 milliseconds, the device may shorten the AV delay to approximately 25 milliseconds or less to create a NPP cycle 504.

When the device 100 shortens the AV delay to create an NPP cycle 504, the paced A waves 510, 512 of the physiologic cycle 502 and the NPP cycle 504 remain in the same relative position within each cardiac electrical cycle, but the evoked response 514 (R wave) of the NPP cycle 504 is shifted in relation to the expected position of the evoked response 516 in a physiologic cycle 502, i.e., is paced to occur abnormally soon after the preceding A wave 512 of the NPP cycle 504 by an increment 518 that may be as great as the entire AV delay. The shift increment 518 in the evoked response 514 due to the shortened AV delay causes a shortened PR interval 520 and a shortened PR segment 522 in the NPP cycle 504.

If the AV delay, which is normally approximately 160 milliseconds long, is shortened enough then hemodynamic imbalances initiated by the NPP cycle 504 cause pumping inefficiency and ineffective filling and ejection. Receptors alert the cardiovascular and/or respiratory control centers of the brain to takes corrective action, including the initiation of a respiratory cycle.

FIG. 6 shows another exemplary comparison 600 of two A–V pacing profiles, a surface ECG representing the application of a physiologic cycle 602 and a surface ECG representing the application of an exemplary NPP cycle 604 of the "transposed wave" type. The term "transposed wave" is used to denote a swap in the positions of two waves within a cardiac electrical cycle. In other words, the desired hemodynamic imbalance is caused by following a paced wave with another wave that normally precedes and initiates the paced wave, all within a single cardiac cycle. This may happen without pacing when in some cardiac pathologies the AV node of the heart assumes its own automaticity instead of being triggered by the sinus rhythm, causing the QRS complex to precede the P wave instead of follow it. It should be noted that the illustrated comparison 600 of two pacing profiles, the ECGs are stylized for descriptive purposes, and that actual ECGs may vary from those shown in FIG. 6.

In the illustrated example, the physiologic cycle 602 has a paced A wave 606 followed by a paced evoked response 608 (R wave). A physiologically normal AV delay, signified by the PR interval 610 and PR segment 612, are maintained within each cardiac cycle by the device 100.

In the exemplary NPP cycle 604 of the transposed wave type, the device 100 transposes the order of the A wave 614 and the evoked response 616 within the cardiac cycle to stimulate the ventricles immediately before stimulating the atria. The device 100 may shift the evoked response 616 to approximately 30 milliseconds before the anticipated paced occurrence of the A wave 614. The wave transposition causes poor or nonexistent pumping and abnormal variances in blood pressure. These abnormalities alert the central nervous system to initiate corrective action, an inventory of the respiratory status and a resumption of breathing. Many types of NPP cycles other than the exemplary shortened AV delay type (NPP cycle 504) and the transposed wave type (NPP cycle 604) can be created by the device 100.

FIG. 7 shows yet another exemplary comparison 700 of two ventricular pacing profiles, a surface ECG representing the application of a physiologic pacing cycle 702 having a native P wave 706 and an ECG representing the application of an exemplary NPP cycle 704 of the shortened AV delay type, but in this case using the stable automaticity of the patient's own SA node to provide a regular sinus rhythm. Since the native P wave 708 occurs naturally, the device 100 sends only ventricular stimuli to pace ventricular contraction within an individual NPP cycle 704 (i.e., "ventricular NPP").

The device 100 shortens the PR segment 710, stimulating an evoked response 712 sooner after the P wave 708 by an increment 714 than in the physiologic cycle 702. Since the atria are not being stimulated by the device 100 in the illustrated example of ventricular NPP, it may not be reliable to attempt to create NPP cycles of the transposed wave type (FIG. 6) using the patient's native sinus rhythm.

Application Patterns for Non-physiologic Pacing Therapy

Figure 8:
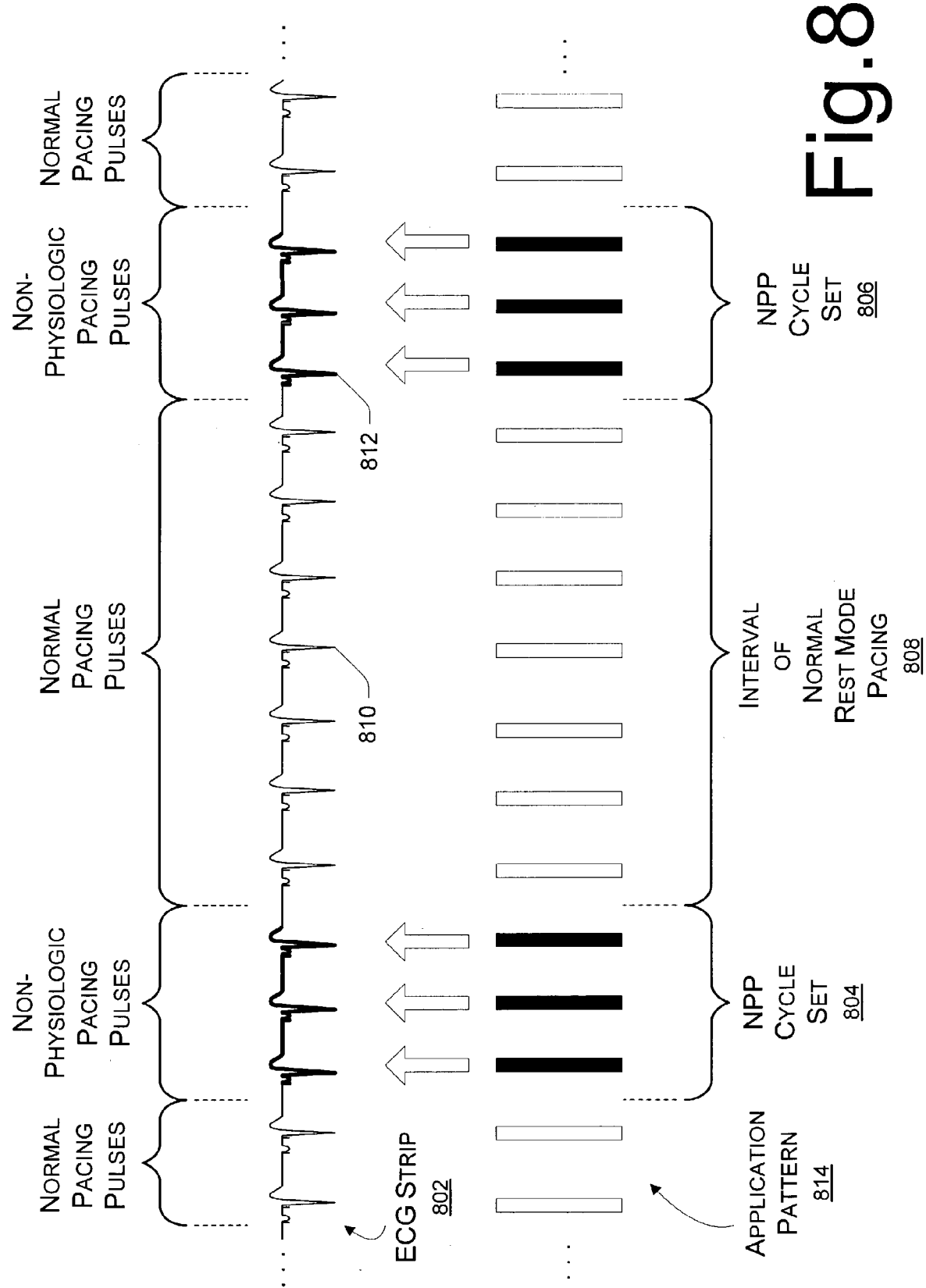
FIG. 8 is a diagrammatic illustration of a first exemplary application pattern for delivering physiologic pacing and exemplary non-physiologic pacing.

FIG. 8 shows an ECG strip 802 illustrating an exemplary implementation of NPP therapy, which comprises NPP cycle sets 804, 806 between intervals of normal rest mode pacing 808. An NPP therapy application pattern 814 shows the relation between the NPP cycle sets 804, 806 and the intervening intervals of normal rest mode pacing 808.

The pulses creating a normal rest mode pacing cycle 810 (i.e., one heartbeat) are physiologically correct, that is, they are pulses that are paced to emulate a normal or "healthy" cardiac rhythm. The pulses comprising an NPP cycle 812 in the illustrated NPP cycle sets 804, 806 shorten AV delay and consequently cause a temporary hemodynamic imbalance. Other types of NPP cycles could be used in NPP cycle sets 804, 806, such as an NPP cycle 604 of the transposed wave type shown in FIG. 6.

Each NPP cycle set 804, 806 typically includes approximately 1 to approximately 20 NPP cycles, the actual number used depending on how the patient's sleep apnea responds to NPP therapy. In some implementations, e.g., in the device 100 using the method of FIG. 4, the number of NPP cycles 812 in a set can be varied during therapy. For example, if the episode of sleep apnea is not responding to NPP therapy, then an exemplary device 100 may increase the number of NPP cycles 812 in each NPP cycle set 802, 804; may administer the NPP cycle sets 802, 804 more frequently (decreased interval of normal rest mode pacing 808 between NPP cycle sets 802, 804); and/or may alter the profiles of the individual NPP cycles 812 being administered. In other implementations, the number of NPP cycles 812 in each NPP cycle set 804, 806 may be static, until changed by a practitioner.

In the illustrated exemplary implementation, three NPP cycles 812 comprise each NPP cycle set 804, 806 separated by intervals of seven physiologic pacing cycles 810. Thus, the ratio of NPP cycles 812 to physiologic cycles 810 is three to seven.

Many "NPP cycle 812 to physiologic cycle 810" ratios may be used, that is, both the interval of normal rest mode pacing 808 between each NPP cycle set 804 and the number of NPP cycles 812 in each NPP cycle set 804, 806 may be adjusted broadly. Exemplary intervals of normal rest mode pacing 808 between NPP cycle sets 804, 806 are approximately between 30 seconds to 2 minutes if the number of NPP cycles 812 in a NPP cycle set 804, 806 is in the range of approximately 4 to approximately 20 NPP cycles 812. For smaller NPP cycles sets 804, 806 consisting of 1–3 NPP cycles 812 per set, an exemplary interval of normal rest mode pacing 808 may be more conveniently measured by the number of heartbeats (physiologic cycles 810) between NPP cycle sets 804, 806. Exemplary values are approximately 5 to approximately 20 heartbeats between NPP cycle sets 804, 806.

Figure 9:
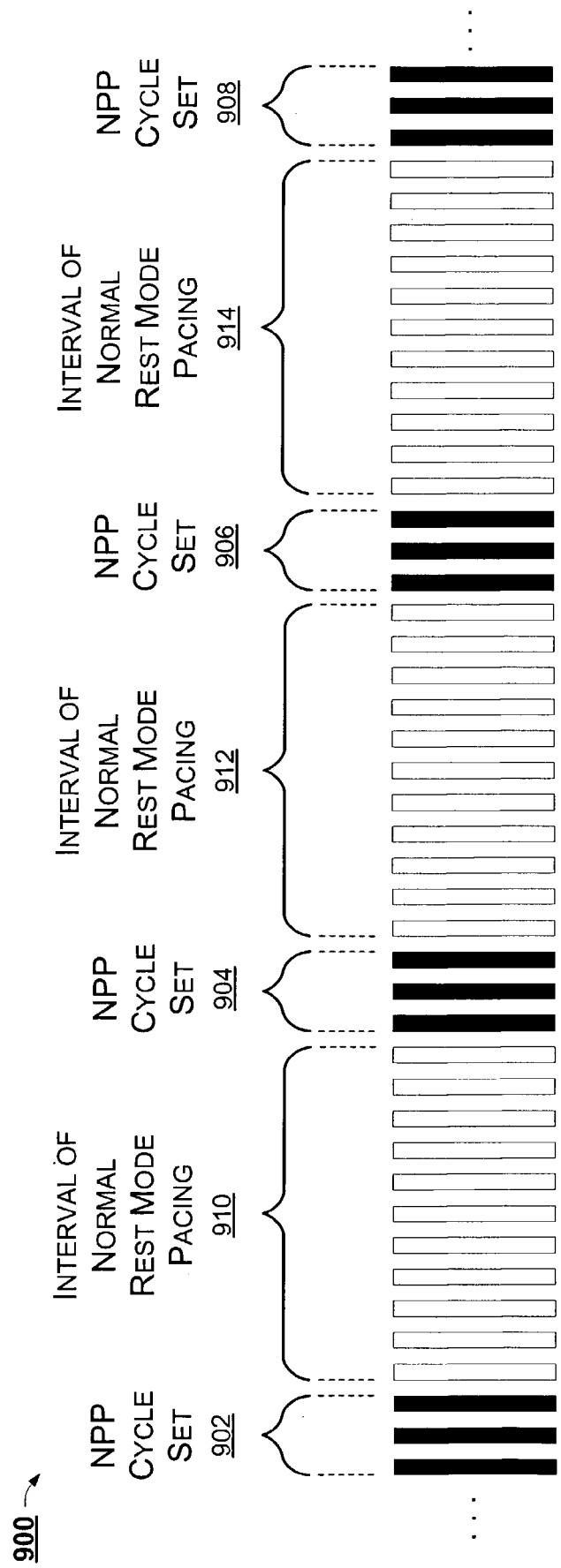
FIG. 9 is a diagrammatic illustration of a second exemplary application pattern for delivering physiologic pacing and exemplary non-physiologic pacing.

FIG. 9 shows another exemplary NPP application pattern 900 having NPP cycle sets 902, 904, 906, 908 that include three NPP cycles 810 apiece. The intervals of normal rest mode pacing 910, 912, 914 each contain eleven physiologic cycles 812. The NPP cycle 812 to physiologic cycle 810 ratio is therefore three to eleven, because of the slightly longer intervals of normal rest mode pacing 910, 912, 914 than those shown in FIG. 8. Relatively high ratios may be used when an episode of sleep apnea is newly discovered by the device 100 and treated aggressively, or when the sleep apnea is recalcitrant. Lower ratios may be used for maintenance, or if feedback indicates the particular patient does not need a very strong NPP therapy.

Figure 10:
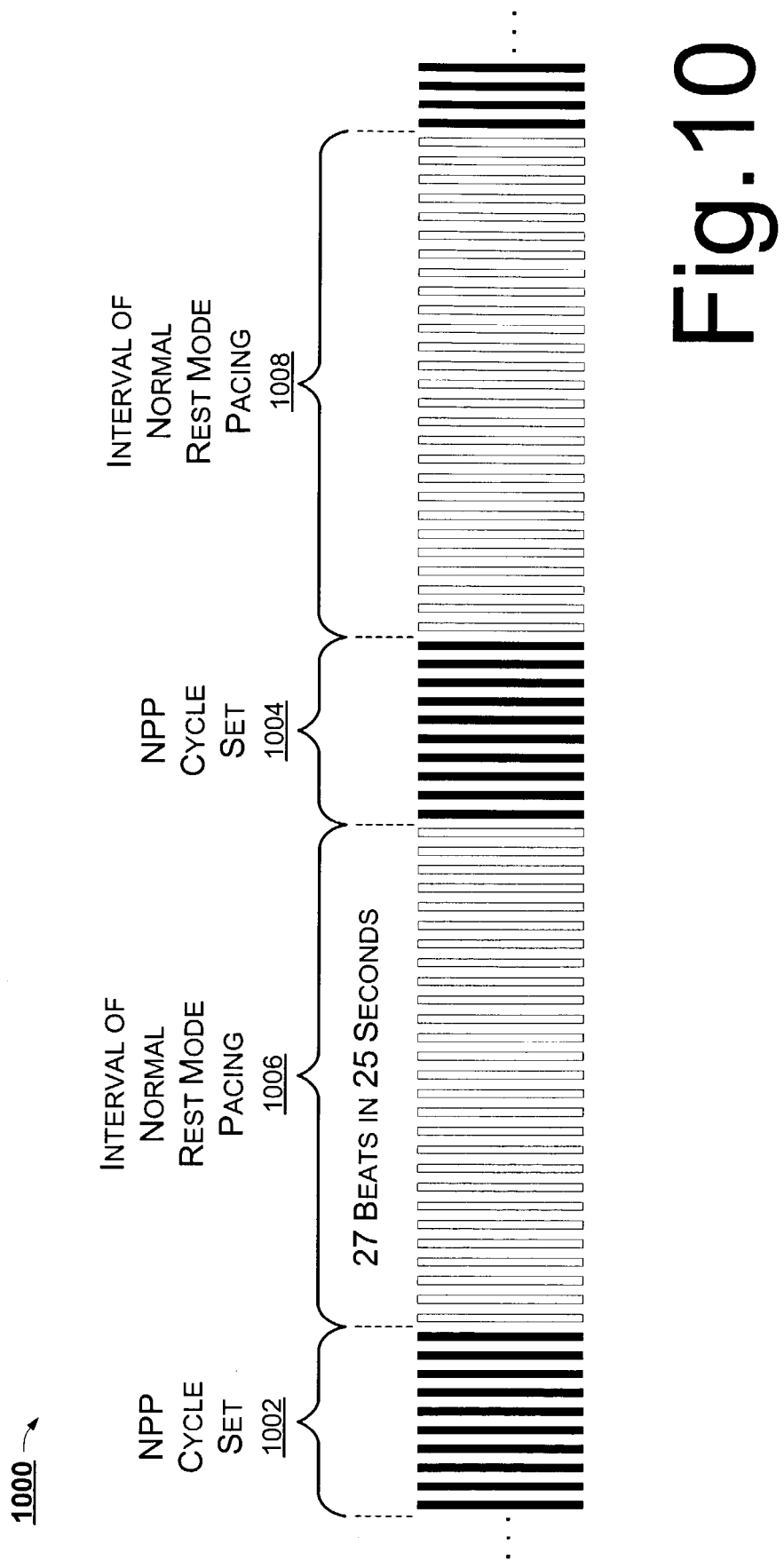
FIG. 10 is a diagrammatic illustration of a third exemplary application pattern for delivering physiologic pacing and exemplary non-physiologic pacing.

FIG. 10 shows still another exemplary NPP application pattern 1000 having NPP cycle sets 1002, 1004 that include x NPP cycles 810 for every y physiologic cycles 812 included in intervals of normal rest mode pacing 1006, 1008. In the illustrated application pattern 1000, there are 10 NPP cycles 810 for every 27 physiologic cycles 812. The ratio of NPP cycles 810 to physiologic cycles 812 may vary if time units are employed to measure the intervals of normal rest mode pacing 1006, 1008 instead of paced or intrinsic heartbeats. For a twenty-five second interval of normal rest mode pacing 1006, 1008, the number of heartbeats in the 25 second interval may vary, thus changing the NPP cycle 810 to physiologic cycle 812 ratio.

The ratio of NPP to physiologic cycles shown in FIG. 10 is relatively close to the ratio shown in FIG. 9. However, the application pattern 1000 is scaled up in FIG. 10 so that sets of NPP cycles 1002, 1004 and intervals of physiologic rest mode pacing 1006, 1008 are each performed for longer intervals. Patients with very severe sleep apnea may require larger NPP cycle sets 1002, 1004 to trigger a central nervous system correction to sleep apnea than patients with mild sleep apnea. In a device 100 using the feedback method shown in FIG. 4, the device can initially apply an application pattern such as that shown in FIG. 10 and then switch to an application pattern such as that shown in FIG. 9 as the patient begins to respond to the NPP therapy. For some patients, an application pattern having small NPP cycle sets of 1 to approximately 2 NPP cycles per set followed by relatively long intervals of physiologic rest mode pacing may be used for maintenance and/or prevention of sleep apnea episodes.

Conclusion

The foregoing discussion describes use of implantable cardiac devices to treat sleep apnea in a patient receiving cardiac pacing therapy. Although the invention has been described in language specific to structural features and/or methodological acts, it is to be understood that 2the subject matter defined in the appended claims is not necessarily limited to the specific features or acts described. Rather, the specific features and acts are disclosed as exemplary forms of implementing the claimed invention.

What is claimed is:

1. A method for treating a patient experiencing sleep apnea, the method comprising:
   detecting an episode of sleep apnea;
   determining one or more parameters for a cardiac pacing pulse, wherein the one or more parameters are selected to create a hemodynamic imbalance within a patient's cardiovascular system; and
   delivering at least one of the cardiac pacing pulses to the patient's heart.

2. The method as recited in claim 1, further comprising applying the cardiac pulse repetitively in sets during a sequence of cardiac cycles, wherein at least one of the cardiac pulses is applied during each cardiac cycle.

3. The method as recited in claim 2, further comprising applying an interval of physiologic pacing pulses between the sets, wherein a physiologic pacing pulse does not aim to create a hemodynamic imbalance.

4. The method as recited in claim 3, wherein each set comprises approximately 1 to approximately 20 cardiac cycles.

5. The method as recited in claim 3, wherein the interval of physiologic pacing pulses is between approximately 30 to approximately 120 seconds.

6. The method as recited in claim 3, wherein the interval of physiologic pacing pulses is approximately 20 to approximately 160 cardiac cycles.

7. The method as recited in claim 3, wherein each set includes between 1 to approximately 20 cardiac cycles and the interval of physiologic pacing is between approximately 30 to approximately 120 seconds.

8. The method as recited in claim 3, wherein each set includes from 1 to approximately 3 cardiac cycles and the interval of physiologic pacing is between approximately 5 to approximately 20 cardiac cycles.

9. The method as recited in claim 1, wherein the cardiac pulse creates a hemodynamic imbalance via a shortened AV delay.

10. The method as recited in claim 1, wherein the cardiac pulse causes an extra contraction of a ventricle in a cardiac cycle.

11. The method as recited in claim 10, wherein the cardiac pulse causes a ventricle to contract before an atrium contracts.

the means for generating non-physiologic pacing pulses comprises means for generating a ventricular stimulation pulse at an atrioventricular delay of less than approximately 25 milliseconds.

12. An implantable cardiac stimulation system comprising:
a pulse generator that generates cardiac pacing pulses for delivery to a patient's heart;
a sleep apnea detector that is operative to detect an episode of sleep apnea; and
a sleep apnea therapy module that is responsive to the episode of sleep apnea to control the pulse generator to generate one or more non-physiologic pacing pulses, wherein the one or more non-physiologic pacing pulses are operative to cause a hemodynamic imbalance within the patient.

13. The system as recited in claim 12, wherein the sleep apnea therapy module applies the cardiac pacing pulse repetitively in sets.

14. The system as recited in claim 13, wherein the sleep apnea therapy module applies intervals of physiologic pulses between the sets, wherein a physiologic pulse does not aim to create a hemodynamic imbalance.

15. The system as recited in claim 14, wherein the sleep apnea therapy module receives feedback from the sleep apnea detector to vary the size of the sets and the size of the intervals.

16. The system as recited in 12, wherein the cardiac pacing pulse creates an abnormal cardiac electrical rhythm and the sleep apnea therapy module receives feedback from the sleep apnea detector to vary the morphology of the abnormal cardiac electrical rhythm.

17. A method for treating a patient experiencing sleep apnea, the method comprising:
detecting an episode of sleep apnea; and
in response to the episode of sleep apnea, delivering a ventricular stimulation pulse at an atrioventricular delay of less than about 25 milliseconds following an atrial event.

18. A method for treating a patient experiencing sleep apnea, the method comprising:
detecting an episode of sleep apnea in a patient; and
applying at least one cardiac pacing pulse to the patient's heart to create a hemodynamic imbalance within the patient's cardiovascular system in response to the detection of an episode of sleep apena.

19. An implantable cardiac stimulation system comprising:
means for detecting an episode of sleep apnea in a patient; and
means for applying at least one cardiac pacing pulse to the patient's heart to create a hemodynamic imbalance within the patient's cardiovascular system in response to the detection of an episode of sleep apena.

20. The implantable cardiac system of claim 19 wherein the cardiac pacing pulse emulates at least part of an abnormal cardiac rhythm.

21. The implantable cardiac system of claim 19 wherein the means for applying at least one cardiac pacing pulse to the patient's heart to create a hemodynamic imbalance within the patient's cardiovascular system comprise means for causing an extra contraction to occur within a subsequent cardiac cycle in response to the detection of the episode of sleep apnea.

22. The implantable cardiac system of claim 21, wherein causing an extra contraction comprises causing an extra ventricular contraction to occur within a subsequent cardiac cycle.

* * * * *